United States Patent
Keltjens

(10) Patent No.: US 7,459,449 B2
(45) Date of Patent: Dec. 2, 2008

(54) STABLE SALTS OF OLANZAPINE

(76) Inventor: Rolf Keltjens, c/o Synthion BV, Microweg 22, 6545 CM, Nijmegen (NL)

( * ) Notice: Subject to any disclaimer, the term of this patent is extended or adjusted under 35 U.S.C. 154(b) by 580 days.

(21) Appl. No.: 11/050,852

(22) Filed: Jan. 27, 2005

(65) Prior Publication Data

US 2005/0272721 A1    Dec. 8, 2005

Related U.S. Application Data

(60) Provisional application No. 60/539,120, filed on Jan. 27, 2004, provisional application No. 60/569,607, filed on May 11, 2004.

(51) Int. Cl.
  *A61P 25/00*    (2006.01)
  *A61K 31/551*    (2006.01)
  *C07D 495/04*    (2006.01)
(52) U.S. Cl. .................... 514/220; 540/557
(58) Field of Classification Search ............... 514/220; 540/557
   See application file for complete search history.

(56) References Cited

U.S. PATENT DOCUMENTS

| | | | |
|---|---|---|---|
| 4,115,568 A | 9/1978 | Chakrabarti et al. | 424/250 |
| 5,229,382 A | 7/1993 | Chakrabarti et al. | 514/220 |
| 5,457,101 A | 10/1995 | Greenwood et al. | 514/220 |
| 5,605,897 A | 2/1997 | Beasley, Jr. et al. | 514/220 |
| 5,736,541 A | 4/1998 | Bunnell et al. | 514/220 |
| 6,063,802 A | 5/2000 | Winterborn | 514/397 |
| 6,348,458 B1 | 2/2002 | Abend | 514/220 |
| 2002/0086993 A1 | 7/2002 | Davies et al. | 540/495 |
| 2004/0265375 A1 | 12/2004 | Platteeuw et al. | 424/464 |
| 2005/0267099 A1 | 12/2005 | Keltjens et al. | 514/220 |
| 2005/0272720 A1 | 12/2005 | Keltjens | 514/220 |

FOREIGN PATENT DOCUMENTS

| | | |
|---|---|---|
| EP | 454436 B1 | 9/1995 |
| EP | 733635 B1 | 8/2001 |
| EP | 831098 B1 | 11/2001 |
| EP | 0828494 | 7/2002 |
| WO | WO 98/11893 | 3/1998 |
| WO | WO 99/16313 | 4/1999 |
| WO | WO 01/47933 A1 | 7/2001 |
| WO | WO 02/18390 A1 | 3/2002 |
| WO | WO 03/007912 A2 | 1/2003 |
| WO | WO 03/091260 A1 | 11/2003 |
| WO | WO 03/097650 | 11/2003 |
| WO | WO 03/101997 A1 | 12/2003 |
| WO | WO 2004/000847 A1 | 12/2003 |
| WO | WO 2004/006933 A2 | 1/2004 |

OTHER PUBLICATIONS

"Anhydrates and Hydrates of Olanzapine: Crystallization, Solid-State Characterization, and Structural Relationships", *Crystal Growth & Design*, 2003, vol. 3, No. 6, pp. 897-907.
"Catalytic Transfer Hydrogenation of Aromatic Nitro-compounds", *Chinese Journal of Pharmaceuticals*, 2001, 32(9), pp. 391-393.

*Primary Examiner*—Brenda L Coleman
(74) *Attorney, Agent, or Firm*—Mark R. Buscher

(57) ABSTRACT

Several salts of olanzapine, including olanzapine malonate, olanzapine glycolate, olanzapine maleate, and olanzapine benzoate, have been found to have favorable solid state characteristics.

22 Claims, No Drawings

STABLE SALTS OF OLANZAPINE

This application claims the benefit of priority from U.S. Provisional Application Ser. No. 60/539,120, filed Jan. 27, 2004, and from U.S. Provisional Application Ser. No. 60/569,607, filed May 11, 2004, the entire contents of each Provisional Application being incorporated herein by reference.

BACKGROUND OF THE INVENTION

The present invention relates to pharmaceutically useful salts forms of olanzapine, pharmaceutical compositions comprising the same and uses thereof.

Olanzapine is a pharmaceutically active compound that can be represented by formula (1).

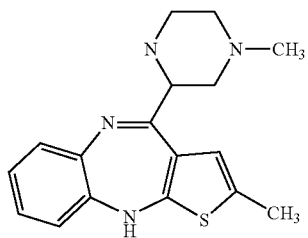

It was disclosed in EP 454436 and corresponding U.S. Pat. No. 5,229,382 as a useful antipsychotic agent. Olanzapine acts as a serotonin (5-HT2) and dopamine (D1/D2) receptor antagonist with anticholinergic activity. In commercially available final forms, the active substance is marketed as a free base, which is a white to yellow crystalline solid that is insoluble in water; i.e., solubility at pH 6.8=0.02 mg/ml.

The olanzapine base is known to exist in various crystalline modifications and in various hydrated forms that are generally stable at ambient conditions; see for example EP 733635 and corresponding U.S. Pat. No. 5,736,541; WO 98-11893; and EP 831098. Having so many different forms is considered to be a disadvantage as repeated production of olanzapine substance may give rise to unpredictable amounts of the respective modifications in the product, which in turn can influence the properties of the product such as in tabletting and/or releasing of the active from the tablets after ingestion.

WO 99-16313 discloses olanzapine pamoate as a pharmaceutical agent. It is a compound that is also insoluble in water and is useful particularly in intramuscular depot forms. However, like the free base, the pamoate salt exists in several forms including hydrates, solvates, and in different counter ion ratios.

WO 03-007912 discloses an amorphous lyophilized olanzapine in a reconstitutable parenteral formulation. The olanzapine is "intimately mixed" with a stabilizer and a solubilizer. The stabilizer is preferably lactose and the solubilizer includes organic acids and most preferably tartaric acid. The composition is formed by lyophilizing, i.e. a type of freeze drying, a solution of olanzapine, the stabilizer and the solubilizer to form the intimate mixture. The resulting lyophilized amorphous product can be reconstituted with parenteral diluents to make an injectable composition. Whether the tartaric acid salt of olanzapine is present in the lyophilized product is unclear.

It would thus be desirable to have a stable, solid form of olanzapine that was resistant to forming solvates. Further, it would be advantageous to have a crystalline form of olanzapine that had improved water solubility.

SUMMARY OF THE INVENTION

The present invention relates to useful salts of olanzapine. In a first aspect, the present invention provides a salt of olanzapine selected from the group consisting of olanzapine malonate, olanzapine glycolate, olanzapine maleate, and olanzapine benzoate. The solid state forms of these salts can show good stability while the malonate, maleate and glycolate salts also show good water solubility.

Another aspect of the invention relates to a pharmaceutical composition comprising a salt of olanzapine selected from the group consisting of olanzapine malonate, olanzapine maleate, olanzapine glycolate, and olanzapine benzoate, and at least one pharmaceutically acceptable excipient. The composition can be a solid dosage form such as a tablet or capsule, etc., or a liquid dosage form such as an oral or injectable solution, among others.

A further aspect of the invention relates to the treatment of various psychological disorders with one of the above salts. For example, a method which comprises administering an antipsychotic effective amount of one of the above olanzapine salts to a patient in need thereof.

Another aspect of the invention relates to a process which comprises reacting olanzapine and a pharmaceutically acceptable acid selected from the group consisting of malonic acid, maleic acid, glycolic acid, and benzoic acid in a solvent to form a pharmaceutically acceptable acid addition salt of olanzapine. The resulting olanzapine salts can be used as active agents in a pharmaceutical composition or as intermediates in the making of olanzapine base.

DETAILED DESCRIPTION OF THE INVENTION

The present invention relates to the discovery of several olanzapine acid addition salts that exhibit relatively stable solid forms, especially crystalline forms, and are not prone to the formation of solvates. These salts are olanzapine malonate, olanzapine glycolate, olanzapine maleate, and olanzapine benzoate; i.e., salts of olanzapine derived from malonic acid, glycolic acid, maleic acid or benzoic acid, respectively. The ratio of acid to olanzapine is not specifically limited, but is typically about 1:1, i.e. usually within +/−0.2. Specific salts of the invention include olanzapine hydrogen malonate, olanzapine hydrogenmaleate, olanzapine monoglycolate, and olanzapine monobenzoate. In this regard, the "hydrogen" prefix with regard to the diacids refers to the fact that substantially only one of the two acid moieties is ionized while the other retains its hydrogen atom, thereby having a ratio of diacid to olanzapine of about 1:1. Similarly, the monobenzoate and monoglycolate refer to the fact that one equivalent of benzoic or glycollic acid is ionized with one olanzapine nitrogen to again form a ratio of acid compound to olanzapine of about 1:1. The salts of the present invention are relatively stable in the solid state. Preferably the solid state salt is a crystalline form and more preferably a non-solvate form including an anhydrate form.

The inventive salts share some useful properties. To begin with, not all olanzapine salts are crystalline solids and/or may be isolated as crystalline solids. For instance, some acids that were proposed in U.S. Pat. No. 5,229,382 such as p-toluenesulfonic acid, naphthalene sulfonic acid or mandelic acid, actually form oily materials and not solids. Also olanzapine dibesylate and olanzapine dimesylate, though being isolateable as a solid, become oily after a short period of storage. Olanzapine tartrate has been isolated as an amorphous material with undefined structure. Thus, some of the generically suggested acid addition salts do not form suitable solid forms or states, unlike the salts of the present invention.

Additionally the inventive salts are not prone to forming solvates. Solvates with organic solvents such as acetone, dichloromethane, dioxane, etc., are inconvenient in pharmaceutical applications because of the toxicity of the solvent. It has been found that acetone forms solvates with many olanzapine salts and these solvates are stable in such respect that the acetone is difficult to be removed even by prolonged drying or at enhanced temperature. A typical example of such a solvate salt is the acetone solvate of olanzapine succinate. The solvent may nevertheless be present in the wet cake of the crude material after isolation in solid state, but a solvent-free product should be obtained by ordinary means of drying. A solvent-free salt (i.e. less than 0.5%, preferably less than 0.1%, of the solvent present) is particularly preferred as the absence of the solvent is advantageous for pharmaceutical applications.

A useful property for an olanzapine salt would be water solubility of at least 1 mg/ml, measured at 20° C., preferably at least 5 mg/ml, more preferably at least 10 mg/ml. Sufficient water solubility provides advantages in making a solid dosage form such as by wet granulation or by spray-drying methods. In these techniques, an aqueous olanzapine salt solution may be used, which is an advantageous as the solution provides a means for obtaining uniform distribution of olanzapine within a solid carrier material, and, after removing the water by drying, provides for a homogeneous material.

Interestingly, however, aqueous solutions of many apparently water soluble salts of olanzapine are not stable. For example, when olanzapine monohydrochloride is dissolved in water at a concentration of 1%, a clear solution is easily formed (the maximum concentration obtainable in the saturated aqueous solution—95 mg/ml—is indeed higher than 1%). However, the solution becomes turbid in a moment and a solid, which is mainly olanzapine base, precipitates from the solution. It is believed that a certain amount of non-protonized olanzapine base is still present in the solution at the pH value that has been inherently adjusted by dissociation of the dissolved salt. If the amount of such non-protonized base is higher than is its solubility threshold at such pH, then the base precipitates. Following the precipitation, the pH of the solution decreases (to more acidic values) until the concentration of non-protonized base at the pH reaches the solubility limit. Then, an equilibrium is maintained and no more free base precipitates. Accordingly, an aqueous solution of solution-unstable (hydrolysable) olanzapine salt may be stabilized by adding sufficient excess of the corresponding acid (or a different acid and/or buffer) to provide a stable solution. These considerations become significant when formulating an aqueous formulation.

The results of testing of many olanzapine salts are summarized in the table below.

| Acid addition salt of olanzapine | Readily isolatable in solid form? | Water soluble at least 10 mg/ml? | Is 1% solution stable from precipitation? | Is the solid state stable? 60° C. | Is the solid state stable? 40° C. 75% RH | Is there low tendency to form solvates? |
|---|---|---|---|---|---|---|
| Monohydrochloride | Yes | Yes | No | Yes | No | No |
| Dihydrochloride | Yes | Yes | Yes | No | No | Yes |
| Hemisulfate | Yes | Yes | No | No | — | No |
| Monosulfate | Yes | Yes | Yes | No | — | No |
| Monomesylate | Yes | Yes | No | Yes | — | No |
| Monoesylate | Yes | Yes | No | Yes | No | Yes |
| Monobesylate | Yes | Yes | No | Yes | No | Yes |
| Mono-L-lactate | Yes | Yes | No | No | — | Yes |
| Hydrogenmaleate | Yes | Yes | No | Yes | Yes | Yes |
| Dimaleate | Yes | Yes | Yes | No | — | No |
| Monobenzoate | Yes | No | — | Yes | Yes | Yes |
| Hemifumarate | Yes | Yes | No | Yes | Yes | No |
| Monoacetate | Yes | Yes | No | No* | — | Yes |
| Monoglycolate | Yes | Yes | No | Yes | Yes | Yes |
| Mono-L-tartrate | Yes | Yes | Yes | No | — | No |
| Di-L-tartrate | Yes | — | — | — | — | No |
| Hydrogenmalonate | Yes | Yes | Yes | Yes | Yes | Yes |
| Hemisuccinate | Yes | Yes | No | Yes | Yes | No |
| Hemiadipate | Yes | Yes | No | No | — | Yes |
| Tosylate | No | — | — | — | — | — |
| Napsylate | No | — | — | — | — | — |
| Mandelate | No | — | — | — | — | — |
| Gluconate | No | — | — | — | — | — |
| Ascorbate | No | — | — | — | — | — |
| Citrate | Yes | No | — | No | — | Yes |
| Dibesylate | Yes** | — | — | — | — | — |
| Dimesylate | Yes** | — | — | — | — | — |
| Pamoate | Yes | No | — | — | — | No |

*converted to free base during study
**not stable at ambient conditions, i.e. decomposition, severely hygroscopic and dissolves in absorbed water, and/or converts to oil.

A dash (-) indicates that the test was not carried out, usually because it was not possible, i.e. if not soluble in water at 1%, then stability of 1% solution was not possible to test. In the above table, a compound that is readily obtainable as a solid is indicated as "Yes" while those that form oils or are severely unstable solid forms are reported as "No." For solubility, 10 mg/ml was tested and if it all dissolved and did not immediately precipitate, then it was considered to meet the solubility. If it failed to all dissolve, it is reported as "No." The solution stability was based on no precipitation from a 1% aqueous solution for at least 12 to 24 hours (i.e., overnight) wherein "Yes" means it was stable—no precipitation. The solid state stability was based on two types of tests: one month at 60° C. and 2-3 months at 40° C. and 75% relative humidity, respectively. A failure was considered to be 1% or more of impurities being formed; i.e. if 1% or more formed, then the salt is reported as "No," not stable, for the corresponding test. The tendency to form solvates was generally determined using acetone as the solvent. The formation of a solvate is indicated as "No," prone to solvate formation.

While each of the salts that are obtainable in a solid state are potentially useful in a pharmaceutical composition, as apparent from the above table, the salts of the present invention advantageously fulfill certain the desired criteria; e.g., good solid state stability and low tendency to form solvates. The salts of the present invention, namely the malonate, glycolate, maleate, and benzoate salts of olanzapine, are generally obtainable as white or almost white, free flowing particulate material especially crystalline material, without odor. They are sufficiently stable against the action of light and an aqueous solution thereof generally provides an inherent pH which is physiologically acceptable.

Specifically, olanzapine hydrogenmalonate is a soluble and stable salt, which is also stable in aqueous solutions. That is, no precipitation occurs from a 1% aqueous solution after 24 hours. This makes olanzapine malonate particularly advantageous for making liquid compositions, especially aqueous dosage forms, as well as solid dosage forms. Olanzapine benzoate is obtainable as a stable crystalline, solvate-free compound that is suitable for making solid dosage forms such as solid oral dosage forms. Because of its low aqueous solubility, it can also be advantageous in making slow or extended release compositions. Olanzapine glycolate and olanzapine hydrogenmaleate are each obtainable as a stable, crystalline, solvate-free compound that is soluble in water. These compounds are useful in making solid dosage forms as well as liquid dosage forms. Because olanzapine glycolate and olanzapine hydrogenmaleate are hydrolysable by water, i.e. they can readily form olanzapine base in aqueous solutions, they are also useful for making special compositions which may liberate olanzapine base at a desired place/time based upon dissolution and/or pH change of an aqueous solution, e.g. in vivo. The stability in aqueous environment of the glycolate and hydrogenmaleate salts may be improved, i.e. the tendency to liberate the olanzapine base may be minimized, by adding sufficient acid into the solution, if desired. If orally ingested, such a solution could be intended to allow hydrolysis of the salt and liberation of olanzapine base in the stomach or intestines, or both, in addition to or instead of absorption of the salt itself into the blood stream.

In addition to the above mentioned properties, the malonate, glycolate, and benzoate salts of olanzapine also exhibit a single endothermic peak on DSC, which means that they do not have a tendency to undergo polymorphic transitions under the action of heat. The malonate, glycolate, maleate, and benzoate solid salts all have a sufficiently high melting point that they do not have a tendency to form oily materials such as during storage or during processing into final forms. And, these salts are generally non-hygroscopic, which is an advantage for long-term storage.

Olanzapine acid addition salts of the invention can be made by conventional acid-base reaction techniques. For example, solid olanzapine salts can be made by a reaction between olanzapine base and the corresponding pharmaceutically acceptable acid in a solvent, and precipitation of the formed salt from the solvent. Suitable solvents include C1-C4 aliphatic alcohols, C1-C6 aliphatic ketones, C1-C6 ethers (incl. cyclic ethers), C1-C6 esters, and hydrocarbons including aromatic hydrocarbons such as toluene. Generally acetone is a preferred solvent. For example, olanzapine base and malonic acid are both soluble in acetone. To the contrary, olanzapine malonate is insoluble in acetone at temperatures close to ambient or lower so that it easily precipitates from an acetone medium. Similarly, another useful solvent is ethanol, with the proviso that olanzapine base is less soluble therein than in acetone. Other useful solvents are ethyl acetate, tetrahydrofuran, and toluene.

Because of the aqueous solubility of olanzapine malonate and olanzapine glycolate, the use/presence of water in the solvent system is generally avoided if precipitation of the salt is desired; i.e. precipitating the water-soluble malonate, glycolate, etc. from a water-containing solvent may be difficult. If precipitation of the water-soluble salt is not desired, then the use of water or mixtures of nonaqueous solvents with water is not particularly limited.

The solubility of starting materials in the solvent may be enhanced by raising the temperature of the reaction mixture, so that the salt forming reaction may proceed at a temperature from ambient to the boiling point of the solvent. Advantageously, the so formed solution of the salt may be treated before precipitation with a suitable adsorption material such as activated charcoal, to remove contaminants.

The solubility of the olanzapine salt in the solvent system may be, accordingly, decreased by cooling the reaction mixture. In general, precipitation of the olanzapine salt is spontaneous at the temperature of salt formation and/or is carried out during or after cooling. In addition, the precipitation may be forced by reducing the volume of the solvent, seeding, adding a contrasolvent or a combination of these techniques.

The olanzapine salt of the present invention may also be prepared from another olanzapine salt (advantageously using differences in solubility of the starting and formed salt in the solvent system) or the acid may be used for the reaction in the form of a salt (e.g. an ammonium salt of the acid).

In making the salt, any form of olanzapine base is suitable as the starting material; including but not limited to "technical grade" olanzapine (this material also comprises solvates of olanzapine with various solvents), olanzapine Form II, olanzapine hydrate, etc.

Furthermore, the olanzapine salt may also be prepared directly from the synthesis of the olanzapine moiety, even without the need of either isolating the olanzapine base or precipitating the olanzapine base. In this case, the starting material for making an olanzapine salt is the reaction mixture comprising olanzapine. For instance, the "des-methyl olanzapine" (2) may be methylated by formic acid/formaldehyde (*Chinese Journal of Pharmaceuticals* 2001, 32, 391-393) to form an olanzapine reaction mixture.

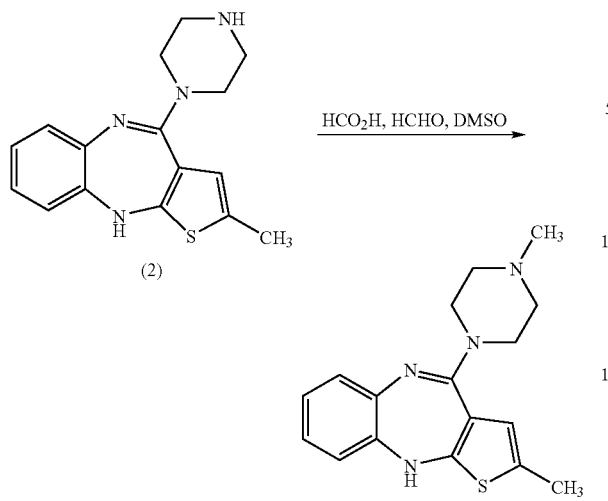

(2)

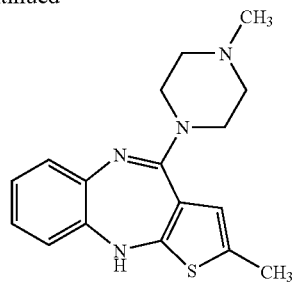

Similarly, the "des-piperazine olanzapine" (3) can be treated with N-methylpiperazine in DMSO under conditions of olanzapine formation to produce a reaction mixture containing olanzapine.

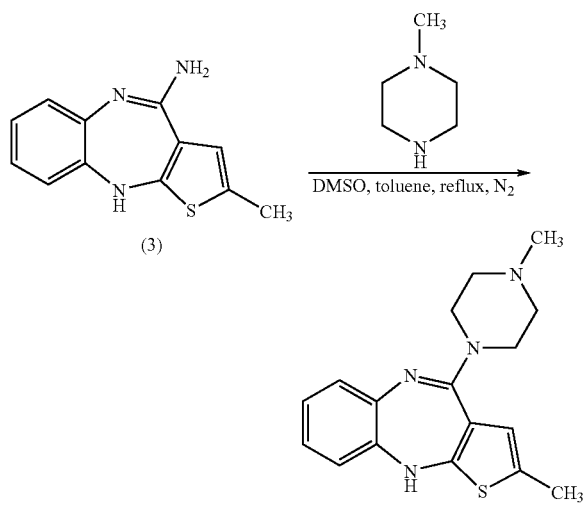

In a third process, the "formyl-olanzapine" (4) is reduced by a reducing agent, for instance by a borohydride agent (WO 2004/000847) or by hydrogen under the presence of a hydrogenation catalyst.

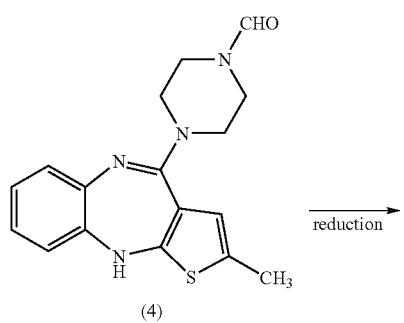

The starting compounds (2), (3), and (4) are known compounds and may be obtained by procedures known in the art.

The reaction mixture, which is not limited to the above three synthetic schemes, is treated with the corresponding acid, for instance maleic acid or benzoic acid, under conditions that olanzapine salt, in this case olanzapine maleate or olanzapine benzoate, is formed. Advantageously, the reaction mixture, before or after contacting with the acid, may be purified from side products or impurities, for instance by filtration, optionally with a surface-active material such as activated carbon or silica, by extraction, by chromatography or by other common means of purification.

For example, in one embodiment, the reaction medium containing the olanzapine can be purified by forming a biphasic organic-aqueous liquid system using water and a water-immiscible solvent, such as ethyl acetate or toluene. The side products and impurities preferentially enter the aqueous phase while the olanzapine preferentially enters the liquid organic phase in a dissolved state. The two phases are separated by partitioning and extracting one layer, generally the aqueous layer phase. The olanzapine-containing organic phase can be further treated to remove contaminants such as by contacting with activated carbon, and/or to remove any water. The purified olanzapine-containing organic solution is then contacted with, e.g., benzoic acid to form olanzapine benzoate, which can be readily precipitated from the organic phase.

In any event, once the salt forming reaction has occured and an olanzapine salt of the present invention has been formed, it can be isolated, typically by precipitation and filtration, etc. The precipitation may be spontaneous, upon cooling and/or may be induced by common means of treating the mixture (e.g. seeding, concentrating the mixture, adding a contrasolvent, etc.). Typically, and preferably, the isolated olanzapine salt is crystalline and substantially free of the solvent from which it was isolated; i.e., it is dry and a non-solvated crystalline salt form of olanzapine malonate, olanzapine glycolate, olanzapine maleate, or olanzapine benzoate. The isolated olanzapine salt can optionally be purified such as by re-crystallization. In the case of olanzapine benzoate, for example, purification can be readily accomplished, if deemed necesary or desireable, by recrystallizating from an aliphatic alcohol such as methanol, ethanol, and/or isopropanol, or from a mixture of an aliphatic alcohol and water.

While the olanzapine salt of the present invnetion can be used as an active agent in a pharmaceutical, alternatively it can be converted to olanzapine base. In this way, the olanzapine salts are useful intermediates for making olanzapine base in any of its anhydrated, hydrated or solvated forms.

Generally conversion includes treating the salt with a suitable alkali, e.g., alkali metal hydroxides including KOH and NaOH, in a suitable solvent, e.g., water, ethanol, toluene, etc., to liberate olanzapine base. The use of an alkali may not be necessary, however. If a water hydrolysable olanzapine salt, such as olanzapine glycolate and maleate, is formed, it can be converted by simply dissolving it into an aqueous solvent. Because the salt is water hydrolysable, the olanzapine base is liberated even without the need of the alkali agent. Regardless of the conversion method, the olanzapine salt can optionally be purified prior to conversion, if desired, such as by recrystallization and/or other conventional purification techniques. The use of an olanzapine salt as an intermediate in forming olanzapine base can be a useful purification technique, which can be applied to the olanzapine reaction mixture or to a previously isolated olanzapine such as technical grade olanzapine.

As mentioned previously, the olanzapine salts of the present invention are suitable for pharmaceutical purposes. The pharmaceutical compositions comprise an olanzapine salt and at least one pharmaceutically acceptable excipient. In a preferred embodiment, the pharmaceutical composition is a dosage form, especially a unit dosage form, that comprises an effective amount of the olanzapine salt of the present invention as the active ingredient and at least one pharmaceutically acceptable excipient. For instance, a suitable pharmaceutical composition may comprise crystalline olanzapine hydrogen malonate in admixture with pharmaceutically acceptable excipient(s).

Pharmaceutically acceptable excipients are known in the art and include carriers, diluents, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, sugars, etc. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Carbopol® (B.F. Goodrich), Eudragit® (Rohm), polycarbophil, and chitosan polymers. Waxes include white beeswax, microcrystalline wax, carnauba wax, hydrogenated castor oil, glyceryl behenate, glycerylpalmito stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

The dosage forms include compositions for parenteral administration, oral administration, rectal administration (e.g., suppository), transdermal administration, and the like. The compositions for oral administration are preferred and may be solid or liquid, such as in the form of an oral solution, oral capsule, or an oral tablet.

Solid compositions for oral administration may exhibit immediate release or modified and/or extended release of the active substance from the composition. The pharmaceutical compositions comprising olanzapine salt may be formulated into normal release tablets, extended release tablets or as rapidly orally disintegrable tablets. For example, the orally disintegrating dosage form may contain silicified microcrystalline cellulose, as disclosed in U.S. patent application Ser. No. 10/824,619, entitled "Orally Disintegrating Tablet," filed Apr. 15, 2004, which is herein incorporated by reference. As another example, the olanzapine malonate may be formulated into rapidly disintegrable tablets similar to those described in U.S. Pat. No. 6,063,802 to WINTERBORN, which is herein incorporated by reference.

The tablets may be produced by any standard tabletting technique, e.g., by wet granulation, dry granulation, melt granulation, or direct compression. In general, the tabletting methods that do not employ a solvent ("dry processes") are preferred because it generally minimizes the formation of impurities.

The dry granulation procedure typically comprises mixing the solid excipients (except lubricants), compacting the mixture in a compactor (e.g., a roller compactor), milling the compacted mass, screening the milled granules, mixing with a lubricant, and compressing the mixture into tablets.

The direct compression procedure generally comprises mixing the solid excipients and compressing the uniform mixture into tablets.

The olanzapine salts of the present invention may also be formulated by melt granulation, i.e., in an admixture with a functional excipient (e.g., glyceryl behenate) that melts at elevated temperature and forms a granulateable melt that is granulated in suitable equipment.

The relative amount of the olanzapine salt in a tablet mass may range from 1 to 10 wt %, such as 2 to 5 wt %.

The olanzapine salt may also be blended into compositions that are suitable for being formulated into pellets by known pelletization techniques. The pellets may comprise olanzapine salts alone with a pellet-forming carrier, or may additionally comprise other excipients such as binders, fillers etc. A plurality of pellets comprising a single dose of olanzapine salts may be encapsulated into capsules made from pharmaceutically acceptable material, such as hard gelatin. In another mode, a plurality of pellets may be compressed together with suitable binders and disintegrants to a disintegrable tablet that, upon ingestion, decomposes and releases the pellets. In yet another mode, the plurality of pellets may be filled into a sachet.

Tablets or pellets may be coated by a suitable film coat, which may be a film coat (dissolvable in the stomach) or an "enteric coat" (not dissolvable in the stomach). Alternatively, the tablets or pellets may be uncoated.

The pharmaceutical dosage forms formulated from the compositions of the invention may comprise a unit dose of olanzapine salt, i.e., a therapeutically effective amount of olanzapine for a single dose administration. The amount of the olanzapine salt, calculated in terms of olanzapine base, in the unit dose may range from 0.1 to 100 mg, more typically 0.25 to 30 mg, preferably from 1 to 20 mg, typically such as 1, 2.5, 4, 5, 7.5, 10, 15 or 20 mg.

The unit dose in tablet form may comprise a single tablet but it may also comprise a divided tablet(s) or several smaller tablets (minitablets) administered at the same time. In the case of minitablets, several smaller tablets may be filled into a gelatin capsule to form a unit dose. The unit dose of pellets in capsule form may comprise a single capsule. The unit dose of the injection solution may be a single vial. Solutions for oral administration may be packed in a multidose package, the unit dose being packaged in a calibrated vessel.

The olanzapine salts of the present invention are suitable to antagonize serotonin and dopamine receptors and have anticholinergic activity. Accordingly, it is useful for preventing, minimizing or reversing the symptoms associated therewith, e.g., in a human subject. This physiological activity indicates that the olanzapine salts are useful to treat, prevent, or ameliorate in animals, especially in humans, symptoms of many psychotic diseases and particularly schizophrenia. In short, any disease or condition that olanzapine is useful in treating or preventing can be treated/prevented by the olanzapine salts of the present invention. Accordingly, the olanzapine salts of the present invention can be used by administering an antipsychotic effective amount of the olanzapine salt to a patient in need thereof. In this regard the various disorders recited in U.S. Pat. Nos. 5,229,382 and 5,605,897 and the amounts to treat them are incorporated herein by reference.

In addition to olanzapine salts, the pharmaceutical compositions of the present invention can also contain other active ingredients, including another olanzapine base or salt.

The present invention is more particularly described and explained by the following examples. It is to be understood, however, that the present invention is not limited to these examples and various changes and modifications may be made without departing from the scope of the present invention.

EXAMPLE 1A

Olanzapine Hydrogenmalonate

To a clear solution of 5.0 g olanzapine base in 150 ml of acetone was added 1.67 g of malonic acid in 30 ml of acetone. The mixture was stirred at 4° C. for 3 hours and the formed crystals were isolated by filtration. Yield 5.15 g (77%); melting point 182-184° C.

EXAMPLE 1B

Olanzapine Hydrogenmalonate

To a hot clear solution of 0.167 g malonic acid in 10 ml of ethyl acetate, was added slowly a clear hot solution of 0.5 g olanzapine free base in 10 ml ethyl acetate. During crystallization, an oil was formed. Continuation of stirring at room temperature resulted in the formation of a yellow solid. After stirring for 4 hours at room temperature, the crystals were isolated by filtration and dried overnight at 50° C. at reduced pressure. Isolated yield: 0.60 gram. $^1$H-NMR showed olanzapine:acid=1:1

EXAMPLE 2A

Olanzapine Benzoate

To a clear solution of olanzapine free base (5.0 g) in acetone (150 ml) was added slowly a solution of 1.0 equivalent of benzoic acid (1.96 g) in acetone (20 ml) at room temperature. After stirring at 4° C. overnight, the crystals were isolated by filtration, washed with acetone (20 ml) and dried overnight at 40° C. Yield: 6.23 g (90%).

EXAMPLE 2B

Olanzapine Benzoate

To a clear solution of 0.196 g benzoic acid in 5 ml ethyl acetate was added slowly a clear hot solution of 0.5 g olanzapine free base in 10 ml ethyl acetate. After complete addition, slowly, the crystallization process started. Stirring at room temperature was continued for 5 hours. The crystals were isolated by filtration and dried overnight at 50° C. in vacuo. Isolated yield: 0.64 gram (92%). $^1$H-NMR confirmed the molar ratio olanzapine: acid=1:1.

EXAMPLE 2C

Olanzapine Benzoate

To a clear solution (50° C.) of 100 g olanzapine free base in 2000 ml ethyl acetate, was added slowly a clear solution of 39.2 g benzoic acid in 250 ml ethyl acetate while stirring mechanically. When almost all benzoic acid was added, the crystallization process started (T=50-55° C.). The mixture was allowed to cool to room temperature while stirring. The pale yellow crystals were isolated by filtration and dried overnight at 40° C. in vacuum. Isolated yield: 130.1 gram (94%). $^1$H-NMR confirms the molar ratio of olanzapine: acid=1:1. DSC: peak at 222.99° C.

EXAMPLE 3

Olanzapine Hemi-Adipate

To a solution of 5.0 g of olanzapine base in 150 ml of acetone a hot solution of 2.34 g of adipic acid in 20 ml acetone was added. The reaction mixture was stirred at 4° C. and the solid was isolated. Yield: 5.33 g

EXAMPLE 4

Olanzapine Hemi-Succinate

To a solution of 5.0 g of olanzapine base in 150 ml of acetone was added, at room temperature, a solution of 1.89 g of succinic acid in a mixture of 50 ml acetone and 5 ml of water. After 5 minutes, crystals appeared, which were filtered off after 2 hours stirring. Yield: 5.0 g (84%)

EXAMPLE 5

Olanzapine Mono-Tartrate 5.0 g of olanzapine base was dissolved in 150 ml of acetone and 2.40 g of L-tartaric acid was dissolved in a mixture of 100 ml acetone and 5 ml water. The solution of the tartaric acid was slowly added to the solution of olanzapine and the mixture was stirred at room temperature for 1 hour and subsequently at 4° C. overnight. Crystals were isolated by filtration and dried overnight at 40° C. in vacuo. Yield: 7.10 g, as a hemiacetonate monohydrate (90%).

EXAMPLE 6

Olanzapine Lactate

To a clear solution of 5.0 g of olanzapine base in 150 ml acetone was added, at room temperature, a solution of 1.44 g of L-(+)-lactic acid in 50 ml of acetone. The reaction mixture was stirred at −20° C. and the solid was isolated. Yield: 3.36 g (52%).

EXAMPLE 7A

Olanzapine Glycolate

To a solution of 5.0 g of olanzapine in 150 ml of acetone was added 1.22 g of glycolic acid in 25 ml acetone slowly at room temperature. The mixture was stirred overnight at 4° C. The crystals were isolated by filtration, washed with 15 ml of acetone and 20 ml of ether and dried overnight at 40° C. in vacuo. Yield: 5.76 g

EXAMPLE 7B

Olanzapine Glycolate

To a clear solution of 75 g olanzapine free base in 1500 ml acetone, was added slowly 18.0 g glycolic acid in 100 ml acetone at room temperature. The resulting mixture was stirred at room temperature overnight. The formed crystals were isolated by filtration and dried overnight at 40° C. in vacuo. Isolated yield: 84.1 gram (90%). $^1$H-NMR confirms the molar ratio olanzapine:acid=1:1.

EXAMPLE 8

Olanzapine Acetate

To a solution of 5.0 g of olanzapine base in 150 ml acetone was added slowly 1.o6 g of acetic acid at room temperature and the mixture was stirred overnight at 4° C. The crystals were isolated by filtration, washed with 20 ml acetone and 20 ml of ether and dried overnight at 40° C. in vacuo. Yield: 3.32 g (56%).

EXAMPLE 9A

Olanzapine Hemifumarate

To a solution of 5.0 g olanzapine base in 150 ml acetone was added slowly a solution of 3.72 g of fumaric acid in 200 ml acetone/40 ml water. Both solutions were mixed at room temperature. The mixture was stored overnight at 4° C. The formed crystals were isolated by filtration, washed with acetone (20 ml) and ether (20 ml) and dried overnight at 40° C. in vacuo. Yield: 4.89 g, as a hemi-acetonate.

EXAMPLE 9B

Olanzapine Hemifumarate

As above, with the proviso that 1.86 g of fumaric acid in 200 ml acetone/5 ml water was used. Yield: 6.16 g, as a hemi-acetonate

EXAMPLE 10A

Olanzapine Hydrogenmaleate

To a solution 5.0 g of olanzapine base in 150 ml of acetone was added a solution of 1.85 g of maleic acid in 25 ml of acetone. After stirring overnight at 4° C., the crystals were isolated by filtration, washed with 20 ml of acetone and 20 ml of ether and dried overnight at 40° C. under vacuum. Yield: 6.16 g (90%).

EXAMPLE 10B

Olanzapine Hydrogenmaleate

To a clear hot solution of 0.5 g olanzapine free base in 10 ml ethyl acetate was added slowly a clear hot solution of 0.185 g maleic acid in 10 ml ethyl acetate. After half of the amount of the acid was added, crystals appeared. After complete addition, the reaction mixture was stirred for 5 hours while the reaction mixture was allowed to cool to room temperature. The crystals were isolated by filtration and dried overnight at 50° C. in vacuum. Isolated yield: 0.65 gram. $^1$H-NMR confirms the molar ratio olanzapine:acid=1:1.

EXAMPLE 11

Olanzapine Besylate

To a solution of 5.0 g of olanzapine in 150 ml acetone was slowly added a solution of 2.8 g benzenesulfonic acid monohydrate in 50 ml acetone at room temperature under stirring. The mixture was stirred 1 hour at room temperature and then at 4° C. overnight. Crystals were isolated by filtration, washed with 20 ml of acetone and 20 ml of ether and dried at 40° C. under vacuum overnight. Yield: 5.98 g (79%).

EXAMPLE 12

Olanzapine Esylate

To a solution of 5.0 g of olanzapine base in 150 ml acetone was added 1.76 g ethane sulfonic acid in 50 ml acetone at room temperature. Immediately a solid started to form. After stirring for 3 hours, the crystals were isolated by filtration and washed with 50 ml acetone. Yield: 6.59 g (97%).

EXAMPLE 13

Olanzapine Mesylate

To a solution of 5.0 g of olanzapine base in 150 ml acetone was slowly added a solution of 1.53 g of methane sulfonic acid in 50 ml of acetone at room temperature. The mixture was stirred for 1 hour and then overnight at 4° C. Crystals were isolated by filtration, washed with 10 ml of acetone and 20 ml of ether and dried overnight at 40° C. in vacuo. Yield: 6.62 g (95%) as a hemi-acetonate.

EXAMPLE 14

Olanzapine Hydrogensulfate

To a solution of 5.0 g olanzapine base in 150 ml acetone was added at room temperature 0.435 ml of 95% sulfuric acid. The mixture was stirred overnight at 4° C. The formed crystals were isolated by filtration, washed with 20 ml of acetone and 20 ml of ether and dried overnight at 40° C. in vacuo. Yield: 5.87 g (approx. 0.25 eq. acetone present).

EXAMPLE 15

Olanzapine Monohydrochloride

To a solution of 5.0 g olanzapine base in 150 ml acetone was added 1.3 ml of concentrated hydrochloric acid at room temperature. The mixture was stirred overnight at 4° C. The formed crystals were collected by filtration, washed with 20 ml acetone and 20 ml of ether and dried overnight at 40° C. in vacuo. Yield: 5.08 g (approx. 0.66 eq. of acetone present).

EXAMPLE 16A

Olanzapine Benzoate by Methylation of Desmethyl Olanzapine

Reaction scheme:

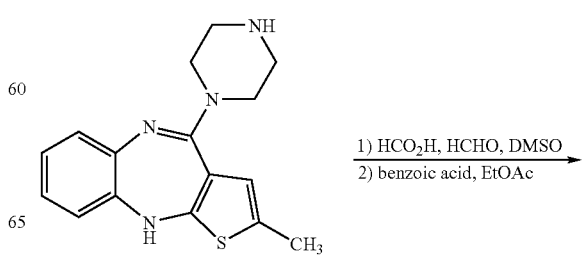

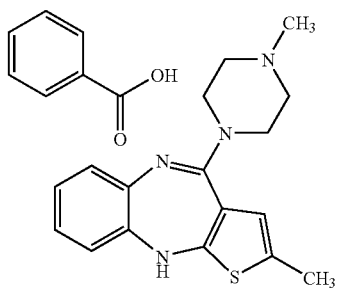

In a 100 ml flask, equipped with a magnetic stirrer, 0.5 g desmethyl olanzapine was dissolved in 5 ml DMSO. Then, 0.142 g formic acid (37% in water) and 0.082 g formic acid (98%) were added and the resulting mixture was heated at 80° C. for 2 hours. After cooling to room temperature, 20 ml ethyl acetate and 20 ml water were added. The organic layer was washed with 2*20 ml water and 20 ml saturated aqueous NaCl, dried ($Na_2SO_4$) and concentrated at reduced pressure to a volume of about 10 ml. Then, 0.200 g benzoic acid dissolved in 2 ml ethyl acetate was added dropwise to the crude olanzapine solution. An off-white/yellow solid formed which was isolated by filtration and dried over weekend at 40° C. in vacuo. Isolated yield: 0.58 gram (80%). $^1$H-NMR: expected compound; trace of ethyl acetate present.

EXAMPLE 16B

Synthesis of Olanzapine and Isolation of Olanzapine as the Benzoate Salt

Reaction scheme:

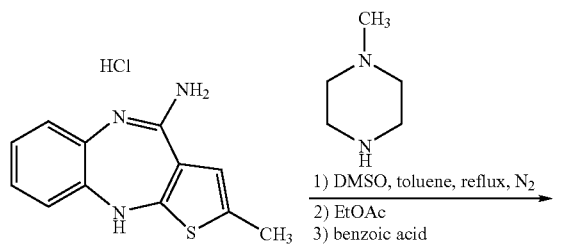

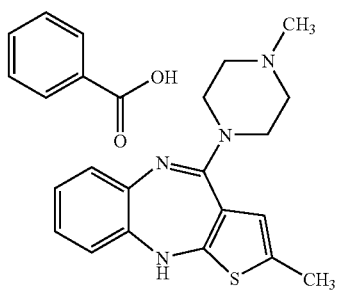

In a 250 ml flask, equipped with a magnetic stirrer, 4.3 g of N-desmethylpiperazine-olanzapine was refluxed in a mixture of 15 ml N-methylpiperazine, 20 ml DMSO, and 20 ml toluene under a nitrogen atmosphere for 20 hours. The mixture was cooled and 50 ml water was added. The aqueous layer was extracted three times with 150 ml ethyl acetate and the combined organic layers were washed 3 times with 100 ml water and once with 100 ml aqueous saturated sodium chloride. After drying over $Na_2SO_4$, the organic layer was concentrated to about 100 ml and 1.6 g benzoic acid was added. After a few minutes, a yellow solid was formed. Stirring was continued at 4° C. for 1 hour. The solid material was isolated by filtration, washed with 5 ml ethyl acetate and 10 ml diethyl ether, and dried overnight at 40° C. in vacuum. Isolated yield: 4.61 g (80%; based on benzoic acid).

EXAMPLE 16C

Synthesis of Olanzapine and Isolation of Olanzapine as the Benzoate Salt

Reaction scheme:

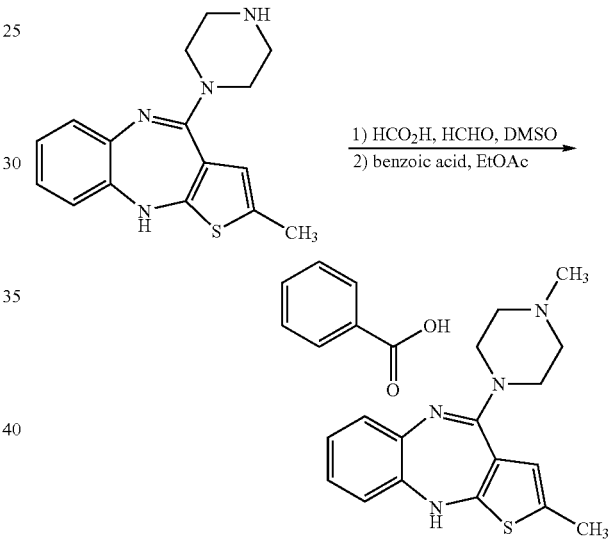

In a 2000 ml flask, 50 g of desmethyl olanzapine was dissolved in 450 ml of DMSO. Then, 13.04 g of formaldehyde (37% in water) and 7.59 g of formic acid (98%) were added and the resulting mixture was heated at 80° C. for 2 hours. The crude reaction mixture was poured into a mixture of 1000 ml of ethyl acetate and 1000 ml of ice-cooled water. The aqueous layer was separated and extracted with 2×500 ml of ethyl acetate. The combined organic layers were washed with 3×500 ml of water and 500 ml of saturated aqueous NaCl, dried ($Na_2SO_4$) and concentrated at reduced pressure to a volume of about 1000 ml. To the warm solution, 20.4 g of benzoic acid was added in one portion under stirring. An off-white/yellow solid was formed. Stirring was continued overnight at room temperature and subsequently for 2 hours at 4 C. The yellow solid was isolated by filtration, washed with 30 ml of cold ethyl acetate and 100 ml of diethyl ether and dried overnight at 60° C. in vacuo. Isolated yield: 60.25 g. Assay (HPLC): 99.1%.

EXAMPLE 16D

Synthesis of Olanzapine and Isolation of Olanzapine as the Benzoate Salt

Reaction scheme:

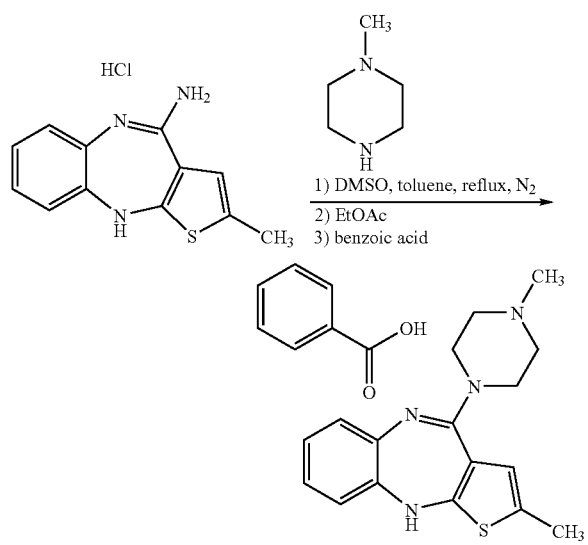

In a 3000 ml flask, 86 g of desmethylpiperazine-olanzapine hydrochloride was refluxed in a mixture of 300 ml of N-methylpiperazine, 400 ml of DMSO, and 400 ml of toluene under a nitrogen atmosphere for 5 hours. The mixture was cooled to 50° C. and poured into a mixture of 2000 ml of ethyl acetate and 2000 ml of ice-cooled water. The aqueous layer was extracted with 2×500 ml of ethyl acetate and the combined organic layers were washed with 3×500 ml of water and with 500 ml of aqueous saturated sodium chloride. After drying over Na$_2$SO$_4$, the organic layer was concentrated to about 1500 ml and 39.6 g of benzoic acid was added in one portion. After a few minutes, a yellowish solid was formed. Stirring was continued overnight at room temperature. The solid material was isolated by filtration, washed with 50 ml of ethyl acetate and 200 ml of diethyl ether, and dried overnight at 60° C. in vacuum. Yield: 86.35 gram.

EXAMPLE 16E

Olanzapine Benzoate from Formyl Olanzapine

Reaction scheme:

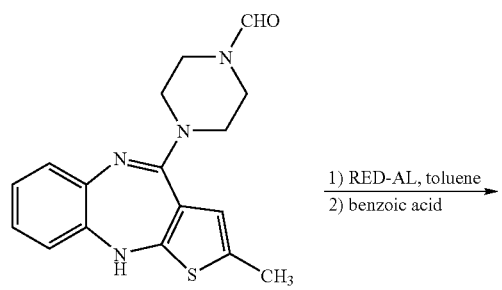

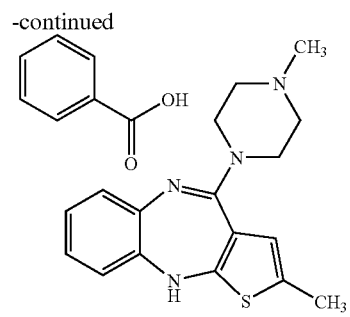

In a 250 ml flask, 3.0 g of N-formyl olanzapine precursor (compound (4)) was suspended in 45 ml of dry toluene and cooled to 0C. Under nitrogen atmosphere, 5.4 ml of Red-Al™ solution (70 wt % solution of sodium dihydrido-bis(2-methoxyethoxy) aluminate in toluene) was added dropwise under stirring. The resulting mixture was allowed to warm up to room temperature. Then 5.0 ml of Red-Al solution was added dropwise at this temperature. After stirring for 5 hours at room temperature, the reaction mixture was poured into 100 ml of water and immediately 100 ml of ethyl acetate was added. The mixture was filtered over a P3-filter to remove insoluble material. The biphasic filtrate was allowed to stand for separating the layers and the aqueous layer was removed and washed with 2×50 ml of ethyl acetate. The combined organic layers were washed with 2×50 ml of water, dried over anhydrous sodium sulfate and concentrated at reduced pressure to a volume of about 50-60 ml. Then, 1.12 g of benzoic acid was added in one portion and the resulting mixture was stirred at 4° C. for 4 hours. The formed solid was isolated by filtration, washed with 5 ml of cold ethyl acetate and 10 ml of cold diethyl ether, and dried overnight at 40 C under vacuum. Yield: 2.75 gram, purity (HPLC): 94.8%.

EXAMPLE 17

Recrystallization of Olanzapine Benzoate

| Experiment | Solvent | Concentration |
| --- | --- | --- |
| A | methanol | 1.8 g/50 ml |
| B | ethanol | 1.4 g/50 ml |
| C | isopropanol | 0.9 g/50 ml |

In three flasks, olanzapine benzoate (purity by HPLC 96.1%) was dissolved in the alcohol solvent at reflux. The hot clear solution was cooled to 10° C. in 2 hours (linear cooling profile) while mechanically stirred. The solid material was isolated by filtration and dried overnight at 40° C. in vacuo.

Results:

| Experiment | yield | purity |
| --- | --- | --- |
| A | 59% | 100.2% |
| B | 77% | 102.2% |
| C | 84% | 96.7% |

EXAMPLE 18

Immediate Release Tablets

The tablet formulations given below are of the core. The tablet core may be coated by conventional filmcoat materials with the proviso that the coating material should not contain polyethylene glycol (due to undesired interaction with olanzapine).

Tablet A

|  | Olanzapine salt | Lactose monohydrate | Hydroxypropyl cellulose | Explotab | MCC | Mg stearate | Total |
|---|---|---|---|---|---|---|---|
| % of tablet | 3.29 | 75.21 | 6 | 5 | 10 | 0.5 | 100% |
| amount/tablet (mg) | 6.58 | 150.42 | 12 | 10 | 20 | 1 | 200 mg |

Tablet B

|  | Olanzapine salt | Lactose anhydrous | Hydroxypropyl cellulose | Explotab | MCC | Mg stearate | Total |
|---|---|---|---|---|---|---|---|
| % of tablet | 3.29 | 75.21 | 6 | 5 | 10 | 0.5 | 100% |
| amount/tablet (mg) | 6.58 | 150.42 | 12 | 10 | 20 | 1 | 200 mg |

Tablet C

|  | Olanzapine salt | Dicalcium phosphate | Hydroxypropyl cellulose | Explotab | MCC | Mg stearate | Total |
|---|---|---|---|---|---|---|---|
| % of tablet | 3.29 | 75.21 | 6 | 5 | 10 | 0.5 | 100% |
| amount/tablet (mg) | 6.58 | 150.42 | 12 | 10 | 20 | 1 | 200 mg |

EXAMPLE 19

Extended Release Tablets

The formulation given below is of the core. Since the olanzapine particles are coated (here with 14% polymer) there shouldn't be a need for an outer tablet coating. If one is still used it preferably should not contain PEG. The amount of coating applied to the particles is usually between 5 and 25% polymer. The content of coated particles in the tablet formulation is usually not more than 70%.

|  | Olanzapine salt | Eudragit NE 30D | Talc | Purified water | Explotab | MCC | mg stearate | Total |
|---|---|---|---|---|---|---|---|---|
| % of coating |  | 12.5[1] | 12.5 | 75 |  |  |  | 100% |
| coated particles (mg) | 6.59 | 3.08 (=0.92 polymer) | 0.92 | 4.94 |  |  |  | 15.53 mg[2] |
| tabletting of coated particles (mg) | 6.59 | 0.92 | 0.92 |  | 5.0 | 86.07 | 0.5 | 100.0 mg |

[1] amount of the polymer
[2] wet coated particles before drying.

EXAMPLE 20

Orally Disintegrating Tablets

| | Tablets D | | | | | | |
|---|---|---|---|---|---|---|---|
| | Olanzapine salt | prosolv HD 90 | L-HPC | Aspartame | Mint flavour | Sodium Stearyl Fumarate | Total |
| % | 6.58 | 83.92 | 5 | 2 | 2 | 0.5 | 100% |
| amount/tablet (mg) | 6.58 | 83.92 | 5 | 2 | 2 | 0.5 | 100 mg |

| | Tablets E | | | | | | | |
|---|---|---|---|---|---|---|---|---|
| | OPN H-malonate | prosolv HD 90 | L-HPC | Avicel CE-15 | Mannitol | Aspartame | Mint flavour | Sodium Stearyl Fumarate | Total |
| % | 6.58 | 38.92 | 5 | 9 | 36 | 2 | 2 | 0.5 | 100% |
| amount/tablet (mg) | 6.58 | 38.92 | 5 | 9 | 36 | 2 | 2 | 0.5 | 100 mg |

EXAMPLE 21

Extended Release Capsules

Pellets/granules are made in a high sheer mixer and later coated. Eudragit is thus both in the core of the granules and on the outside.

Granule Filled ER-Capsule.

| | Olanzapine salt | MCC 101 | Eudragit L30 D-55 | Talc | Triethyl-citrate | Purified water | NaOH/HCl | Total |
|---|---|---|---|---|---|---|---|---|
| % of pellet core | 2.03 | 83.431 | 5.09[1] | 5.09 | 0.509 | 3.85 | q.s. | 100% |
| amount/pellet core(mg) | 6.58 | 270.68 | 16.51 | 16.51 | 1.65 | 12.49 | q.s. | 324.43 mg |
| % of coating | — | — | 66.67 | 26.67 | 6.66 | — | — | 100% |
| Amount/pellet core(mg) | — | — | 21.63 | 8.65 | 2.16 | — | — | 32.44 mg |
| Total mass pellet formula: | | | | | | | | 356.87 mg |

[1]polymer

EXAMPLE 22

Injections

Lyophilized Powder for Im-Injection.

| | Olanzapine salt | lactose monohydrate | hydrochloric acid | sodium hydroxide | water |
|---|---|---|---|---|---|
| Amount (mg/mL) | 6.58 | 33 | qs | qs | to 1 mL |

Solution for Im-Injection.

| | Olanzapine salt | hydrochloric acid | sodium hydroxide | water |
|---|---|---|---|---|
| amount (mg/mL) | 6.58 | qs | qs | to 1 mL |

EXAMPLE 23

Oral Liquids
Oral Liquid.

|  | Olanzapine salt | hydrochloric acid | sodium hydroxide | Mint flavor | sodium saccarin | methyl paraben | propyl paraben | water |
|---|---|---|---|---|---|---|---|---|
| Amount (mg/mL) | 6.58 | qs | qs | 2-20 drops per 10 mL | 6 | 0.16 | 0.1 | to 1 mL |

All of the patents mentioned above are incorporated herein by reference in their entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

I claim:

1. A salt of olanzapine selected from the group consisting of olanzapine malonate, olanzapine glycolate, and olanzapine benzoate.

2. The salt according to claim 1, which is olanzapine hydrogen malonate.

3. The salt according to claim 1, which is olanzapine monoglycolate.

4. The salt according to claim 1, which is olanzapine monobenzoate.

5. The salt of olanzapine according to claim 1, wherein said salt is crystalline.

6. The salt according to claim 5, which is substantially free from an organic solvent.

7. A pharmaceutical composition comprising said salt according to claim 1 and at least one pharmaceutically acceptable excipient.

8. The composition according to claim 7, wherein said composition is a solid form.

9. The composition according to claim 7, wherein said composition is a liquid form.

10. The composition according to claim 9, which further comprises an acid.

11. A method, which comprises administering an antipsychotic effective amount of the olanzapine salt according to claim 1 to a patient in need thereof.

12. The method according to claim 11, wherein said effective amount of olanzapine salt is within the range of 0.25 to 30 mg, expressed in terms of the weight of the free base.

13. A process which comprises reacting olanzapine and a pharmaceutically acceptable acid selected from the group consisting of malonic acid, glycolic acid, and benzoic acid in a solvent to form a pharmaceutically acceptable acid addition salt of olanzapine.

14. The process according to claim 13, which further comprises precipitating said salt of olanzapine from said solvent.

15. The process according to claim 14, which further comprises isolating said salt of olanzapine as a solvent-free salt.

16. The process according to claim 15, wherein said solvent is acetone.

17. The process according to claim 14, which further comprises converting said acid addition salt olanzapine to form olanzapine free base.

18. The process according to claim 17, which further comprises purifying said addition salt of olanzapine prior to said converting to olanzapine free base.

19. The pharmaceutical composition according to claim 7, wherein said salt is olanzapine benzoate and said excipient comprises anhydrous dibasic calcium phosphate.

20. The pharmaceutical composition according to claim 19, wherein said composition further comprises hydroxypropyl cellulose.

21. The pharmaceutical composition according to claim 19, wherein said composition is an uncoated tablet.

22. The pharmaceutical composition according to claim 20, wherein said composition is a tablet tat was made by direct compression.

* * * * *